(12) United States Patent
Maness et al.

(10) Patent No.: US 6,633,822 B2
(45) Date of Patent: Oct. 14, 2003

(54) VIBRATION DATA PROCESSOR AND PROCESSING METHOD

(75) Inventors: Philip L. Maness, El Cajon, CA (US); Johannes I. Boerhout, La Mesa, CA (US)

(73) Assignee: SKF Condition Monitoring, San Diego, CA (US)

( * ) Notice: Subject to any disclaimer, the term of this patent is extended or adjusted under 35 U.S.C. 154(b) by 0 days.

(21) Appl. No.: 09/912,224

(22) Filed: Jul. 23, 2001

(65) Prior Publication Data

US 2002/0038187 A1 Mar. 28, 2002

Related U.S. Application Data

(62) Division of application No. 09/056,155, filed on Apr. 6, 1998, now Pat. No. 6,275,781.
(60) Provisional application No. 60/054,084, filed on Jul. 29, 1997, provisional application No. 60/054,085, filed on Jul. 29, 1997, and provisional application No. 60/063,022, filed on Oct. 23, 1997.

(51) Int. Cl.[7] .................. G01R 23/16; G01H 17/00; G06F 19/00
(52) U.S. Cl. .................................... 702/56; 702/34
(58) Field of Search .................. 702/56, 34, 35, 702/36, 39, 183, 184, 185, 77; 708/300, 303, 400, 404, 406

(56) References Cited

U.S. PATENT DOCUMENTS

| | | | |
|---|---|---|---|
| 4,520,674 A | 6/1985 | Canada et al. | |
| 4,607,529 A | 8/1986 | Morey | |
| 4,862,407 A | 8/1989 | Fette et al. | |
| 4,885,707 A | 12/1989 | Nichol et al. | |
| 4,929,874 A | 5/1990 | Mizuno et al. | |
| 4,991,107 A | 2/1991 | Sloane | |
| 5,068,799 A | 11/1991 | Jarrett, Jr. | |
| 5,233,546 A | 8/1993 | Witte | |
| 5,255,565 A | 10/1993 | Judd et al. | |
| 5,258,923 A | 11/1993 | Imam et al. | |
| 5,317,524 A | 5/1994 | Das et al. | |
| 5,445,028 A | 8/1995 | Bianchi et al. | |
| 5,446,917 A | * 8/1995 | Krisciunas et al. | 708/313 |
| 5,453,744 A | 9/1995 | VanDeusen et al. | |
| 5,477,730 A | 12/1995 | Carter | |
| 5,582,192 A | 12/1996 | Williams, III | |
| 5,633,811 A | 5/1997 | Canada et al. | |
| 5,679,900 A | 10/1997 | Smulders | |
| 5,825,657 A | 10/1998 | Hernandez | |
| 5,870,699 A | * 2/1999 | Canada et al. | 702/113 |
| 5,943,634 A | 8/1999 | Piety et al. | |
| 6,004,017 A | 12/1999 | Madhavan | |
| 6,026,348 A | 2/2000 | Hala | |
| 6,101,453 A | 8/2000 | Suwa et al. | |
| 6,275,781 B1 | * 8/2001 | Maness et al. | 702/182 |
| 6,351,714 B1 | * 2/2002 | Birchmeier | 702/145 |

FOREIGN PATENT DOCUMENTS

WO   WO 95/30134   11/1995

OTHER PUBLICATIONS

Crystal Semiconductor Corporation Databook, "CS4215 16–bit Multimedia Audio Codec", pp. 4–29, Sep. 1993.*

* cited by examiner

*Primary Examiner*—Patrick Assouad
(74) *Attorney, Agent, or Firm*—Knobbe, Martens, Olson & Bear, LLP

(57) ABSTRACT

A vibration data processor and processing method uses a frequency domain filter having low pipeline delay and accurate time domain signal reconstruction. The filter may be user configurable, and the filter may receive input data from a variable number of decimation stages. Sequences of extracted vibrational features are routed to a variable length output buffer for event detection.

15 Claims, 7 Drawing Sheets

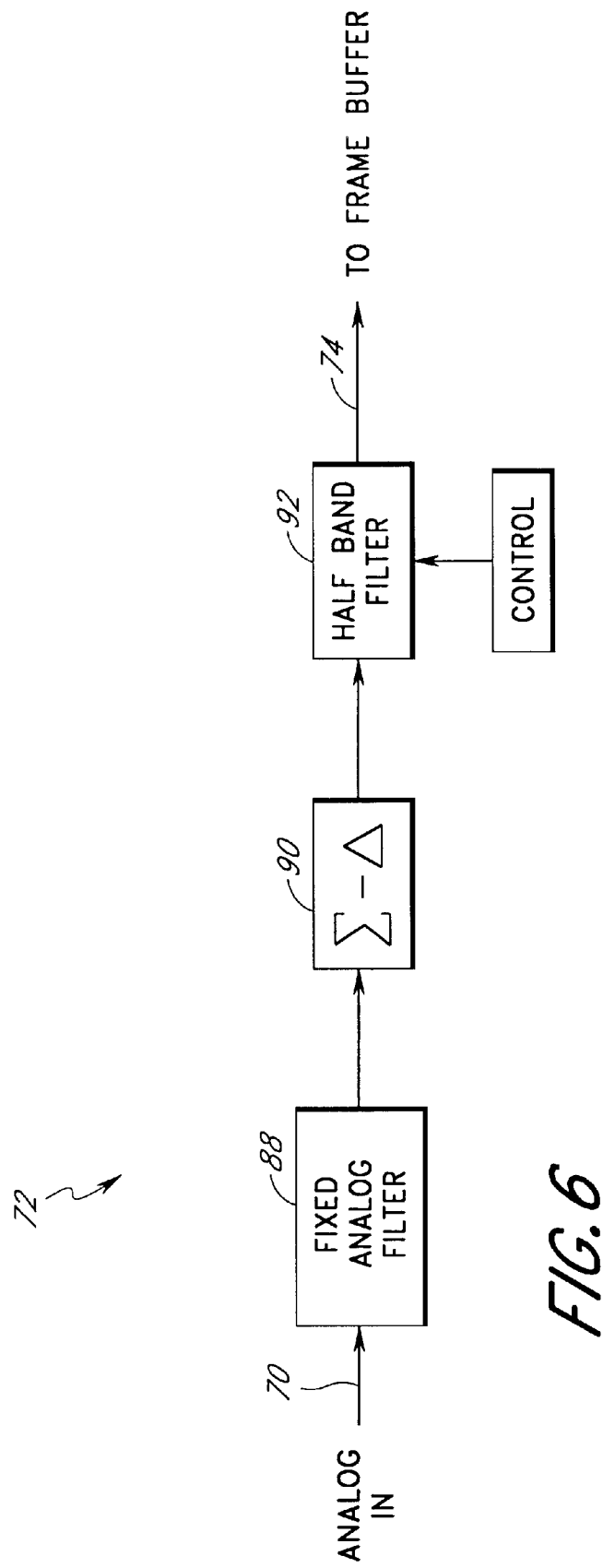

VIBRATION DATA PROCESSOR AND PROCESSING METHOD

CROSS REFERENCE TO RELATED APPLICATIONS

This application is a divisional of and claims priority to U.S. application Ser. No. 09/056,155, filed on Apr. 6, 1998, now U.S. Pat. No. 6,275,781, and entitled Vibration Data Processor and Processing Method. This application also claims priority under 35 U.S.C. § 119(e) to the following U.S. Provisional Patent Applications: Ser. No. 60/054,084 entitled Condition Monitoring Apparatus, filed Jul. 29, 1997; Ser. No. 60/054,085 entitled Vibration Data Processor and Processing Method, filed Jul. 29, 1997; and Ser. No. 60/063,022 entitled Digital Vibration Data Processor, filed Oct. 23, 1997. The disclosures of each of these applications are hereby incorporated by reference in their entireties.

BACKGROUND OF THE INVENTION

1. Field of the Invention

The present invention relates to methods and apparatus for the collection, processing, and analysis of vibration data from rotating machinery.

2. Description of the Related Art

Rotating industrial machinery is present in a wide variety of environments, including petrochemical plants, power production plants, pulp and paper mills, and others. Because shutting down these machines for maintenance or as the result of component failure may involve considerable expense in lost production, preventive vibration monitoring of such machines is routinely performed. In general, vibration levels in selected frequency bands are monitored and measured on a given machine, and defects in bearings or other rolling elements may be detected before catastrophic failure occurs. With these techniques, maintenance may be efficiently scheduled. With the detection of more extreme vibration levels, the machine may be automatically shut down via relay actuation.

Vibration data processing and event detection in systems such as these was traditionally done with analog circuits, which do not lend themselves to intelligent data processing algorithms. With the advent of relatively low cost digital technology, digital signal processing and analysis has also recently been applied in these environments. In most cases, however, a large amount of analog signal conditioning and filtering is necessary. Depending on the frequency band or bands of interest, different analog filters were utilized and tuned to select desired passbands for subsequent conversion to digital data and analysis. A system of this nature is illustrated in FIG. 1. In this type of system, a host event detector 10 (which may be analog or digital in nature) is connected to a variable analog filter 12, which in turn receives an electrical signal from a transducer 14 on a machine 16 being monitored, the analog filter 12 must be rather complex and requires some type of user control 18. To be configurable for use with different machines having variable characteristic vibration frequencies. In past systems, therefore, providing a customer with tailor made vibration monitoring solutions was cumbersome and costly due to the large amount of configurable analog circuitry.

Digital signal processing techniques have been proposed to replace some or all of the traditional analog conditioning and filtering. Using a digital signal processor (DSP) to perform the required processing will hopefully allow a much more flexible system yet maintain good filter performance. U.S. Pat. No. 5,633,811 to Canada et al. describes a vibration monitoring system which uses a single fixed analog low pass filter and performs additional filtering with digital techniques. U.S. Pat. No. 5,477,730 to Carter discloses a vibration monitoring system incorporating a digital interference filter.

Although digital vibration data processing has been proposed, high quality filtering in the digital domain has not been performed accurately and efficiently. Prior art systems have also failed to address a fundamental issue in any vibration monitoring system. That is, the delay between event occurrence and event detection by the system. As the digital processing takes time, there is inevitably some delay between the moment when the analog signal appears at the input of the system, and when the processed digital representation of that signal is available for analysis. In the implementation of prior art systems such as those described in Canada or Carter above, efforts at minimizing this delay would result in further reductions in the filter quality or increases in the cost of the system to the point where its use is no longer economically feasible. There is thus a need for efficient vibration data processing and analysis methods which minimize processing time without sacrificing filter performance and without requiring excessively costly signal processing capabilities.

SUMMARY OF THE INVENTION

The present invention includes a vibration monitoring system comprising a digital filter having a time domain input coupled to an output of an analog to digital converter and a time domain output coupled to an input of event detection circuitry. The filter may have a pipeline delay of less than approximately 100 milliseconds. In advantageous embodiments, the filtering is performed in the frequency domain by a single chip digital signal processor having a maximum throughput of less than approximately 10,000,000 computations per second per channel, and wherein each channel is sampled at at least approximately 25.6 KHz.

In another embodiment, the invention comprises a vibration data processor comprising a frequency domain filter for filtering digital samples of a vibration transducer signal and a mask generator coupled to the frequency domain filter for creating and storing filter masks used by the frequency domain filter. Mask generation may be under user control. Accordingly, one embodiment further includes a user input device coupled to the mask generator for user specification of one or more frequency response characteristics of the frequency domain filter. Additional forms of user control may also be included in embodiments of the invention. Thus, the invention may include a vibration data processor comprising a pre-processor with a user selectable number of decimation stages, a user configurable frequency domain filter, and a reconstruction buffer of user selectable length. Other embodiments additionally comprise an accumulator of user selectable depth coupled between the frequency domain filter and the reconstruction buffer.

BRIEF DESCRIPTION OF THE DRAWINGS

FIG. 6 is a block diagram of the preprocessor of FIG. 5A.

DETAILED DESCRIPTION OF THE PREFERRED EMBODIMENTS

Preferred embodiments of the present invention will now be described with reference to the accompanying figures, wherein like numerals refer to like elements throughout. The terminology used in the description presented herein is not intended to be interpreted in any limited or restrictive manner simply because it is being utilized in conjunction with a detailed description of certain specific preferred embodiments of the present invention.

Figure 1:
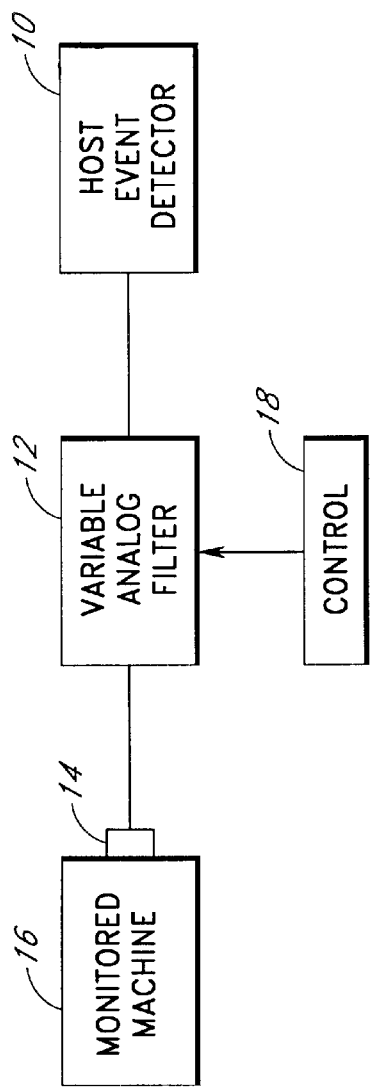
FIG. 1 is a block diagram of a prior art analog vibration monitoring system.
Figure 2:
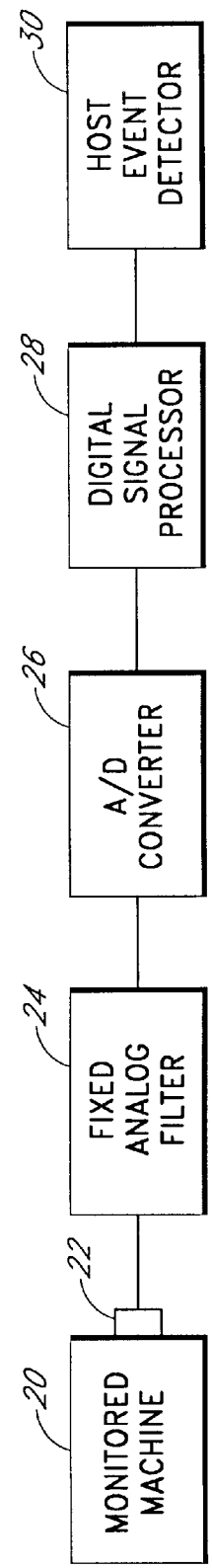
FIG. 2 is a block diagram of a digital vibration monitoring system.

Referring now to FIG. 2, a high level block diagram of a digital vibration monitoring system in accordance with the invention is presented. The system comprises a monitored machine 20 having an attached transducer 22 which senses and converts mechanical parameters into analog electrical signals. A wide variety of transducer types are well known in the art, including eddy current position sensors, piezoelectric accelerometers, etc. Any mechanical to electrical signal converter may be used with the present invention and is encompassed by the term "transducer".

The analog electrical signal output from the transducer 22 is routed to an analog low pass filter 24 having a fixed upper cutoff frequency. Advantageously, this analog filter 24 need not be configurable, as further filtering is performed digitally in later stages of the system as will be explained in detail below. Because of subsequent filtering, this analog filter 24 may have a high frequency cutoff of 150 kHz for example, even though the frequency bands of interest when monitoring most rotating machinery are below approximately 10 kHz.

The analog signal is then converted to a series of digital data samples by an analog to digital converter 26, and the set of data samples are routed to a digital signal processor 28. The digital signal processor 28 filters the digital signal to remove energy present in undesired frequency bands to produce a filtered and conditioned digital signal. Parameters of this digitally filtered and conditioned signal (such as peak and/or rms amplitude) are monitored by the host system 30 to detect evidence of malfunction, excessive wear, etc.

Figure 3:
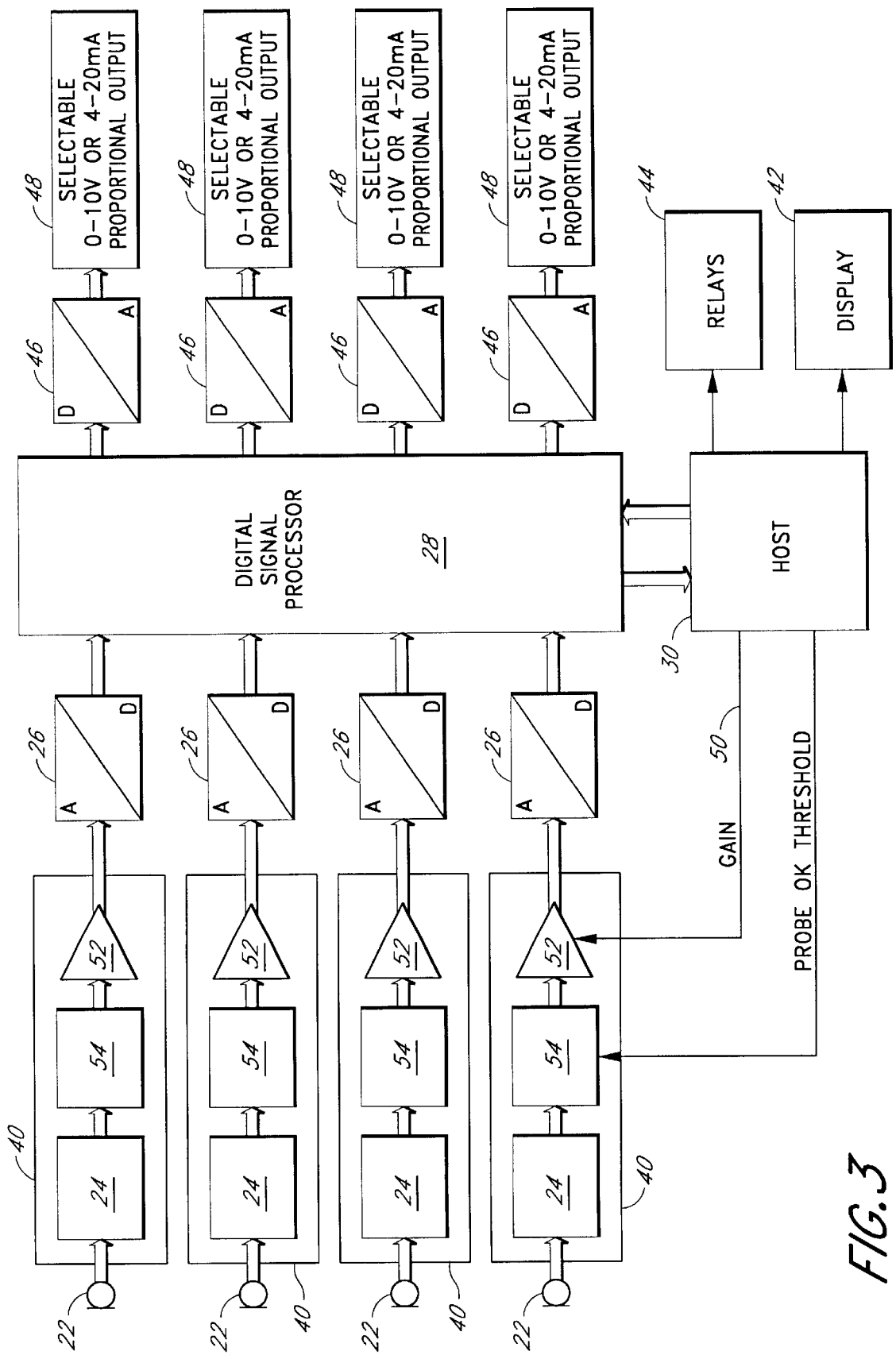
FIG. 3 is a block diagram of a first specific embodiment of a digital vibration monitoring system.

One embodiment of the general scheme set forth in FIG. 2 is illustrated in FIG. 3. The monitoring system of FIG. 3 includes four separate monitoring channels, each of which includes the transducer 22, analog filtering 24, an analog to digital converter 26, a digital signal processor 28, and host event detector 30 which are also illustrated in FIG. 2.

It is one advantageous aspect of the system of FIG. 3 that at least some of the analog portion of the signal preprocessing is performed by circuitry which is present on a daughterboard module 40, which is mounted on a motherboard. The motherboard thus includes connectors for removably mounting the daughterboards. In these embodiments, the motherboard will also have the A/D converters 26 and digital signal processor 28 mounted thereon, usually in a permanent fashion. These features are advantageous because current protection systems have limited modularity with respect to the acquisition and conditioning of data signals from sensors or transducers. Current users of machine monitoring systems have very little choice in which transducers can be used with a given multiple-channel board, and even worse, most monitoring systems do not allow a given channel to accept different sensor or transducer types (i.e., channel A must always be an eddy probe input, channel B must always be a velometer input, etc.).

This system illustrated in FIG. 3 eliminates these limitations by incorporating the motherboard-daughterboard concept, wherein the daughterboards may be. handmountable to daughterboard mounts on the motherboard. In some embodiments, the motherboard contains the conversion, some analog, and digital circuitry, and the daughterboards contain the analog signal conditioning circuitry necessary prior to digitization. Although a given daughterboard may comprise input interface circuitry specific to a given transducer type, the daughterboards may use a standard output interface to the motherboard, allowing them to be interchangeable between channels. This means that any transducer specific daughterboard can be used on any channel, and can coexist on a motherboard with any other daughterboard type.

As shown in FIG. 3, each daughterboard makes up a single channel. The input transducer signals enter the motherboard and are routed onto a respective daughterboard. The daughterboards 40 condition the analog input signals such that maximum resolution and accuracy is obtained without saturating the input to the analog to digital converters 26.

Each channel can accept any type of daughterboard, and therefore any of several types of transducer inputs, allowing users complete flexibility in configuring the system to their application. Thus, each input channel may be characterized as a "universal input" channel. It may be appreciated that daughterboards may be configured to include two or more separate and independent channels.

The host processor 30 performs several control and analysis functions. It may output a gain control signal 50 for a digitally controlled analog amplifier 52 on the daughterboards. The host 30 may also control a window comparator 54 which is used to detect probe faults. This probe fault circuitry is described in more detail in U.S. Provisional Application Ser. No. 60/054,095, entitled "Fast Probe Failure Determination" filed on Jul. 29, 1997, and in co-pending U.S. patent application of the same title filed on the same date as the present application. The disclosures of both of these applications are hereby incorporated by reference in their entireties. As mentioned above, once overall vibration parameters have been calculated by the digital signal processor, they may be downloaded to the host processor 30, which may display the measured parameter values or alarms based thereon to equipment operators via an LED or other type of display device 42. The host may also be configured to actuate relays 44 in response to the measured parameter values to directly control some or all of the monitored machinery.

It may also be desirable to output analog signals representative of the parameter values to other monitoring equipment. This may be performed by digital to analog conversion circuitry 46 which receives one of the measured vibration parameter values as an input, and has as an output a current or voltage signal 48 proportional to the digital input value.

The digital to analog converters and analog to digital converters may comprise commercially available audio codecs, such as the 16 bit model CS4215 available from Crystal Semiconductors (a division of Cirrus Logic). These codecs are dual-channel, CD quality stereo A/D and D/A converters, and are based on sigma-delta conversion technology. With the sigma-delta architecture, 64× oversampling results in avoiding complicated analog-based anti-aliasing filters prior to digitization. The codecs also allow the four channels to be sampled simultaneously, eliminating the need for a multiplexer to switch between channels before making a conversion. The codecs have a standard high-speed serial interface to the digital signal processing circuitry 28. The digital signal processing circuit 28 receives digitized signal data via this serial interface, and performs various filtering, detection, and other functions. A wide variety of digital signal processors are commercially available and are suitable for use in the present invention. In one embodiment, the signal processing and primary feature extraction functions are performed on a Motorola 56002 single chip digital signal processor (DSP). The 56002 may be configured to process four (4) channels in real time, and as will be explained in more detail below, may be configured to generate a filtered time domain output signal segment for each channel every 30 ms.

Figure 4:
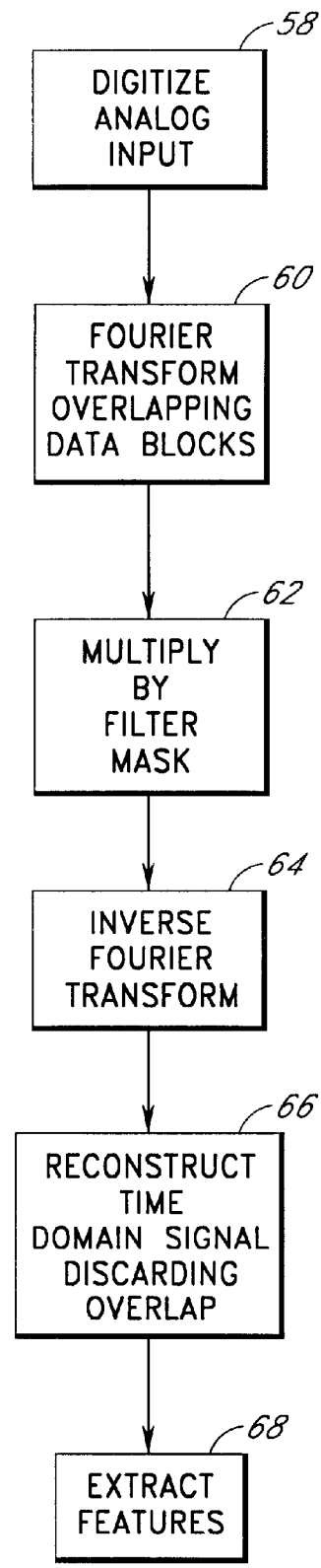
FIG. 4 is a flowchart illustrating a mode of operation of the digital vibration monitoring system of FIG. 3.

With reference to FIG. 4, one embodiment of a vibration data filtering method in accordance with the invention will now be described. To increase filter flexibility, it is advantageous to perform the signal processing, from the sensor interface to the desired output, in the digital domain. This preferably includes both filtering and feature extraction functions. Thus, the input vibration signal is first digitized at block 58. In one suitable embodiment, the filter bandwidth is from 0 to 10 kHz, and digital samples are output from the A/D conversion circuitry at a rate of 25.6 kHz. This 0–10 kHz range meets a wide variety of machine monitoring applications. Of course, bandwidths including higher frequencies may also be used, as long as the samples are produced at or above the Nyquist frequency for the upper limit of the desired band. As mentioned above, the digitization block 58 may advantageously be performed with input oversampling sigma-delta A/D converters, so that higher frequency components of the input signal are not aliased into the 0 to 10 kHz band of interest.

The technique chosen to implement the digital filter is a frequency domain convolution method. The general technique is referred to in most signal processing literature as the overlap and save frequency domain convolution method. Referring to block 60 of FIG. 4, overlapping frames of time domain data are sequentially Fourier transformed into sets of frequency domain data. At block 62, each frequency domain data set is multiplied by a filter mask function to attenuate the undesired frequency bands. At block 64, the sets of filtered frequency domain data are sequentially inverse Fourier transformed into frames of filtered time domain data. A filtered time domain output signal is then reconstructed at block 66, discarding the overlapping portions of the filtered data frames. At block 68, vibrational features are extracted from the filtered time domain digital data. These extracted feature may include peak or RMS accelleration or velocity, two channel calculations such as orbit monitoring, or any type of vibration parameter of interest in a given application. Using these extracted features, events are detected such as excursions of the peak acceleration over a user selected setpoint.

The digital filter preferably performs both highpass, notch, bandpass, and lowpass filtering over the maximum possible range of the 0–10 kHz input. Selectable highpass and lowpass corner frequencies should therefore be as close to 0 and 10 kHz as possible. The noise floor should be minimized without substantially affecting the available filter range. Execution should be in real time and should be fast enough that no input data gets missed or skipped. In addition, the delay through the filter should be minimized so that vibration events at the input of the monitoring system are detected by the system as soon as possible, preferably within 100 ms, to meet important industry standards such the American Petroleum Institute No. 670. Additional desirable features for the filter are arbitrary corner frequency selection, and arbitrary shape, such as any combination of highpass, lowpass, bandpass and notch filtering.

Figure 5A:
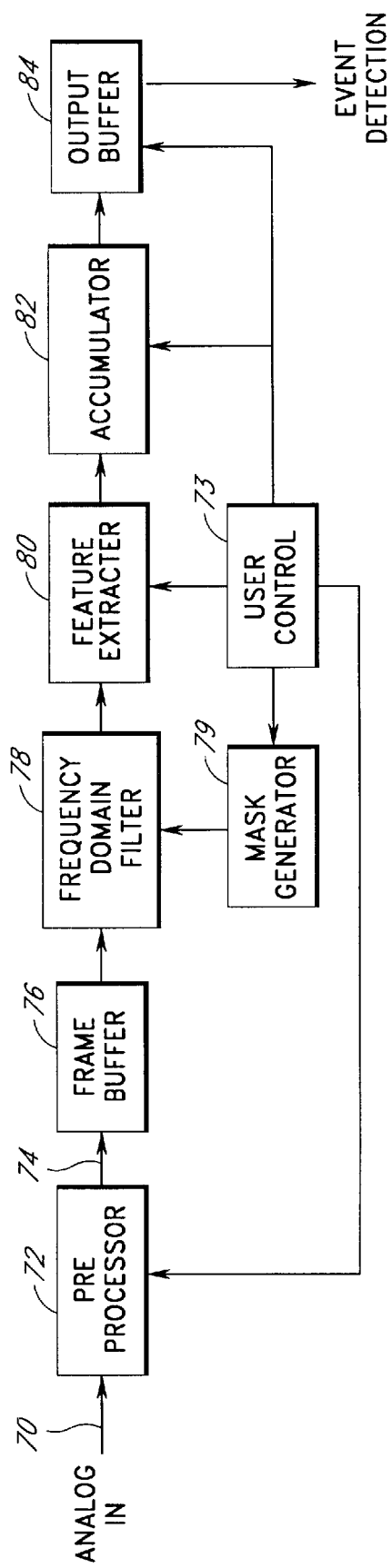
FIG. 5A is a block diagram of a data path in a digital vibration monitoring system in accordance with the invention.
Figure 7:
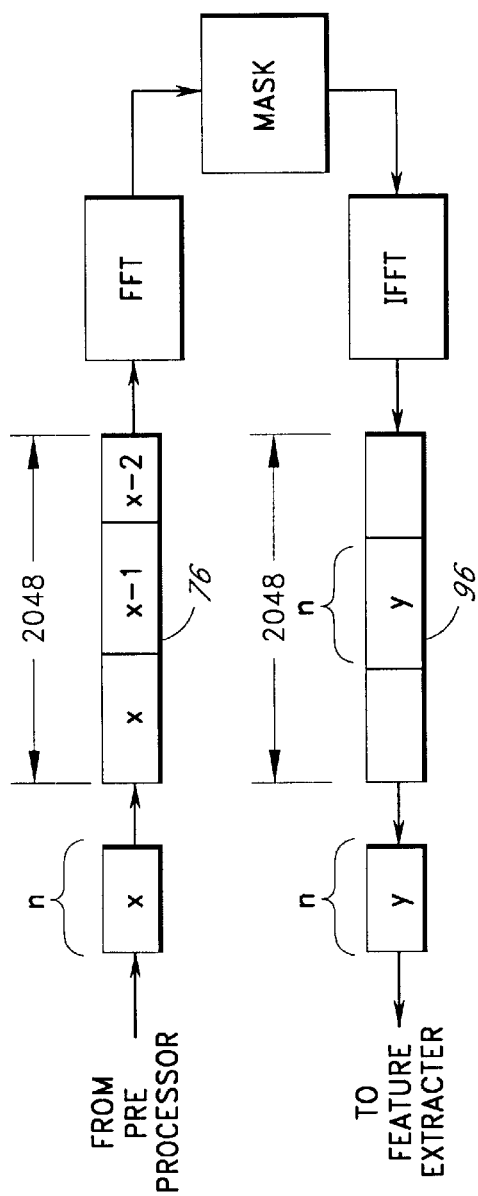
FIG. 7 is a block diagram of the frequency domain filter of FIGS. 5A and 5B.

The signal-processing data path of one embodiment is illustrated in additional detail in FIGS. 5 through 7. As is illustrated in FIG. 5A, the analog vibration signal 70 is routed to a pre-processor circuit, which advantageously includes data decimation as will be explained in more detail below with reference to FIG. 6. The pre-processor 72 may be connected to a user control input device 73 such as a keypad or other well known user I/O device which may be provided as part of the host monitoring system 30. With this user control, variable decimation is possible depending on the frequency bands of interest in the vibration signal.

The output 74 of the pre-processor circuit comprises a stream of digital samples of the input analog signal 70 at a rate of 25.6 kHz if no decimation is performed in the pre-processer. If decimation is performed by the pre-processor, this 25.6 kHz sample output rate will be divided by $2^n$, where n is the number of decimation stages selected by the user. These digital samples are queued in a circular frame buffer 76 with new input data sequentially overwriting the oldest data in the buffer. At defined intervals, the content of the frame buffer 76 is routed to a frequency domain filter 78 described in more detail with reference to FIGS. 7 and 8. During filtering, the frequency domain data in multiplied by a filter mask representative of the desired filter frequency response. Accordingly, a mask generator 79 creates the appropriate mask for use by the frequency domain filter. The mask generator 79 is also preferably under the control of the user via the user control input device 73 as described above with reference to the pre-processor 72. The user may therefore control mask generation by selecting, for example, desired pass or stop bands for the frequency domain filter 78.

Following frequency domain filtering, a time domain data block is routed to a feature extracter 80. The feature extracter 80 performs computations on the filtered time domain data block, such as selecting the peak value, calculating an RMS value, or performing any of a number of calculations so as to extract vibrational features of interest from the filtered signal. The feature extracter 80 may advantageously calculate several features of interest on each data block. The feature extracter 80 may also receive input data blocks from two separate channels, and calculate an orbit or other dual channel feature of interest in vibration monitoring.

Extracted features are then routed to one or more accumulators 82, each of which has an output connected to a circular output buffer 84 . As additional time domain data blocks are output from the frequency domain filter 78, they are processed by the feature extracter 80 and the results are forwarded to the accumulators 82. As one simple example, the feature extracter could select the peak value in the data block, and calculate an RMS value from the data block. Each of these extracted features would be routed to a separate accumulator 82 dedicated to one particular extracted feature. Sequential sets of these extracted feature data points are concatenated together in the accumulators 82 and the output buffers 84 for analysis by the system. It will be appreciated that any number of accumulators 82 and output buffers 84 may be provided depending on the number of features of interest for the given system being monitored. The accumulator 82, output buffer 84, and feature extractor 80 are advantageously coupled to the user control input 73 respectively. The user may therefore control the calculations performed by the feature extracter. Additionally, the user may control the depth of the accumulators 82 and length of the output buffers 84 in accordance with the frequency bands of interest being monitored, as is explained further below with reference to FIG. 5B. Event detection is performed by analyzing the data held in the output buffers 84. Although not illustrated in FIG. 5A, the filtered time domain data blocks output from the frequency domain filter 78 may also be routed to a digital to analog converter in addition to the feature extrater 80. This allows the visual display of the filtered output signal.

Figure 5B:
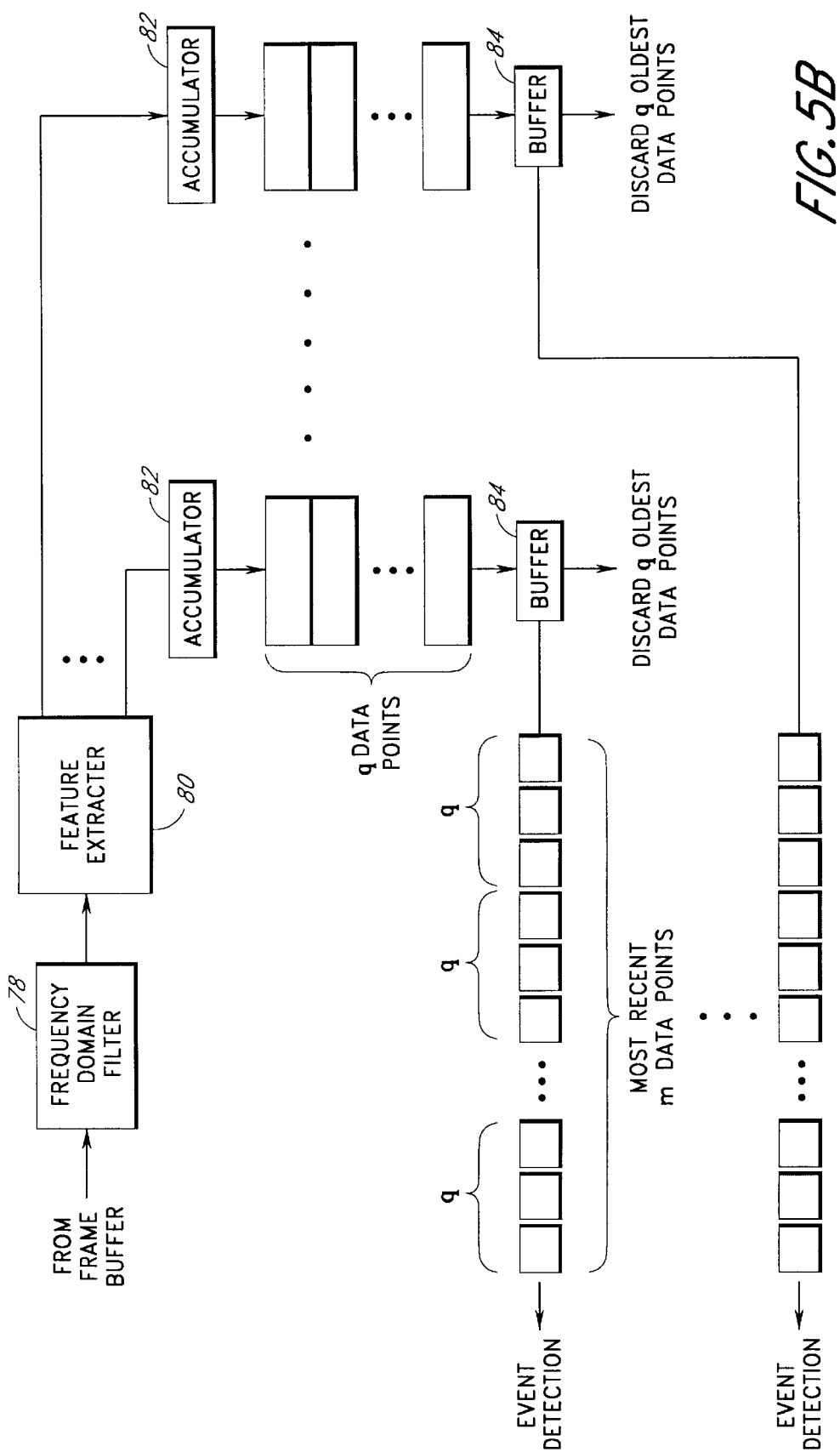
FIG. 5B is a block diagram illustrating data flow through the accumulators of FIG. 5A.

FIG. 5B illustrates a feature extracter 80 having multiple outputs feeding a plurality of accumulators 82, wherein each accumulator stores a selected type of extracted feature data. Referring additionally now to this Figure, each accumulator 82 stores a user preselected number, q, of data points output from the feature extracter 80 prior to having its contents flushed to its respective output buffer 84. The length of the output buffer is also advantageously of user selectable length, so as to concatentate a second number, m, of data points, wherein m is advantageously an integer multiple of the q data points periodically received from the accumulator 82. These m data points are then analyzed for calculating overall peak, rms, and other vibration parameters of interest over time periods which may be longer than that represented by the single data blocks processed by the feature extracter 80.

It is one aspect of the invention that filtering and reconstruction is performed on a fixed time basis rather than on a fixed data length basis. Although the number of samples present in the frame buffer 76 on which the frequency domain filtering is performed is fixed, the frequency domain filter 78 performs the filtering operation on the data present in the frame buffer 76 at fixed time intervals, regardless of how many new data points have entered the frame buffer 76 during that time interval. In one suitable embodiment, the time interval is 30 ms. Thus, in this embodiment, every 30 ms, n raw data samples enter the input frame buffer 76, and a filtered block of n data samples is forwarded to the feature extracter 80. Also, every 30 msec an extracted feature is forwarded to each accumulator 82 from the feature extracter. How many samples are in this block of n is dependent on the effective signal sample rate, as will be described below in conjunction with FIG. 6.

As mentioned above, the accumulators 82 may store a user selectable number of data points. If the accumulation depth is equal to an integer q, the accumulator 82 will wait to acquire q extracted feature data points before forwarding this set of q data points to the output buffer 84. The content of the output buffer 84 is therefore updated every q times 30 ms in this embodiment. When the output buffer 84 receives the q new data points, the oldest q data points currently in the buffer 84 are overwritten.

The output buffer 84 may have a length m, which is advantageously an integer multiple of the accumulation depth q. The stored series of extracted features which is present in the output buffer 84 thus represents m times 30 ms of filtered input vibration data. In one suitable embodiment of the invention, q is user selectable from 1 to 255, and m is user selectable from 2 q to 64 q. With a 30 msec block length, the longest representation of time domain signal storable in each output buffer 84 is 489.6 seconds, and under these circumstances the output buffer 84 will be updated every 7.65 seconds. The lowest frequency that can be accounted for in the resulting over-all value is directly related to the length of the buffer from which it is computed. For example, if a buffer contains 0.1 second worth of data, the lowest frequency that can be reliably detected is 10 Hz. With a maximum length of almost 490 seconds of data, characteristic vibration frequencies as low as approximately 0.002 Hz may be detected and analyzed with this system.

The adjustable accumulation depth and output buffer length result in increased system flexibility. The output buffer length represents the number of blocks of data points which are used to represent the time domain segment which is analyzed by the host monitoring system. The accumulator increases the number of extracted feature data points in each block. Increases in both allow lower frequencies to be detected. Decreasing ouptut buffer length results in reduced retention time in the buffer, clearing it more quickly of transients which the user may wish to ignore.

FIGS. 6 and 7 illustrate signal pre-processing and frequency domain filtering in detail. FIG. 6 illustrates the pre-processor 72 portion of the circuit. Referring now to FIG. 6, the analog vibration signal is first routed through a fixed low pass analog filter 88 having an upper cutoff frequency of, for example, approximately 150 kHz. The analog signal is then digitized with a sigma-delta analog to digital converter 90. As discussed above, the sigma-delta converter may advantageously output data samples at a rate of 25.6 kHz, essentially free of aliased signals in the 0–10 kHz band. The signal pre-processing stage may additionally comprise a decimation/half band filter 92, which may be controlled to include a variable number of decimation by 2 stages, with appropriate anti-aliasing filtering using half band filters. In one specific embodiment, up to seven decimation stages may be selected by the user, decimating by a factor of 2 to 128 in steps of $2^n$. This layer of processing occurs during the sample acquisition interrupt of the DSP. The pre-processor output 74 goes to the input frame buffer 76.

It may be appreciated that the number of new points in each sequential filtered frame will depend on the number of decimation stages during pre-processing, which affects the ultimate effective rate of sample acquisition by the frame buffer. At an initial nominal sampling rate of 25.6 kHz, the input frame buffer 76 receives 768 new samples every 30 msec if no decimation is performed. This number will be divided by 2 for every operative decimation stage. Thus, if 7 decimation stages are selected, 6 new samples will enter the input frame buffer 76 in every 30 ms window.

Data flow through the input frame buffer 76 and the frequency domain filter 78 is illustrated in FIG. 7. As shown in this Figure, in one embodiment of the invention, the input frame buffer 76 is configured as a circular buffer which is 2048 samples long. During data acquisition, n samples representing a 30 msec time period "x" of vibration data are sequentially loaded into the buffer, overwriting the oldest n samples. In the specific example shown in the Figure, no decimation has been performed. In this configuration, the number of samples, n, in a 30 msec period is 768. After the 768 samples of period "x" are loaded, data from period "x" occupies a 768 address block of the frame buffer, data from the last preceding period "x−1" occupies an adjacent 768 address block, and a 512 sample portion of the second preceding 30 msec period "x−2" resides in the next adjacent address block to fill the 2048 sample frame buffer.

After this 30 msec, 768 sample block has been loaded, a copy of the content of the frame buffer is Fourier transformed into the frequency domain, using well known fast Fourier transform (FFT) techniques. This produces a 2048 bin frequency domain data set which is multiplied by a filter mask which will be described in more detail below. The filtered data set is inverse Fourier transformed to produce a 2048 filtered sample output frame 96 of time domain data. From this ouptut buffer, the centrally located n filtered samples are selected for routing to the feature extracter 80, and the remainder of the data in the output frame buffer 96 is discarded.

As decimation stages are added during pre-processing, the number of samples loaded into the input frame 76 in each 30 msec period is decreased. Operation is unchanged, however. A number of samples, n, are loaded into the input frame buffer in a 30 msec period. The 2048 sample frame buffer is frequency domain filtered, and the n centrally located samples of the output frame buffer 96 are routed to the feature extracter. If no decimation is performed, n is 768. If 7 decimation stages are used, n is six.

The sequential processing of input frames on a fixed time basis has several advantages. First, the time period may be chosen in conjunction with the maximum sample rate and frame buffer sizes to guarantee adequate overlap in the signal reconstruction in the accumulator 82 and output buffer 84. Accurate signal reconstruction requires that the centrally located sample set forwarded to the accumulator be no more than, and preferably less than, approximately ½ of the total size of the ouptut frame. For example, with a 2048 sample frame, reconstruction should be performed with at most about 1024 samples at a time. At a 25.6 kHz sample rate, this is 40 msec worth of data. Thus, processing on a 30 msec time period allows sufficient time to complete the frequency domain filtering process with relatively inexpensive signal processing hardware, while still guaranteeing adequate overlap during time domain signal reconstruction. As decimation stages are added, the number of samples in each 30 msec period decreases, thereby providing increases in reconstruction overlap.

Additionally, by processing at fixed time intervals, advantage may be taken of certain properties of the FFT, which allow the processing of two separate input frame buffers simultaneously. One distinct advantage of this is a simplified data path and processing time advantage. Another advantage of this simultaneous two channel processing is simplified data management in calculations involving related channels. Two channel measurement processes are common is vibration analysis and monitoring applications, such as when two sensors are mounted to a single bearing journal, in an 'X' and 'Y' position.

In performing this process, two separate input buffer frames from independent channels of the system are mathematically treated as the real and imaginary part of a constructed single time domain function to be Fourier transformed. Following the transform, the Fourier transforms of the separate channels can be computed from the real and imaginary parts of the transform of the constructed single time domain function. The inverse Fourier transform is performed in the same fashion, by constructing another complex frequency domain function, transforming that back to the time domain, and separating the contribution from the separate channels. The mathematics of this procedure are well known, but their application to multi-channel vibration data processing is made especially convenient by the fixed time processing of the invention. This is because both channels will be ready for processing the same time, regardless of whether or not the number of decimation stages being used in each channel, and thus the effective sample rate for each channel, is the same or different.

The delay in this system, once the initial pipeline is full, can easily be calculated. The worst case delay in generating the "overall", (i.e. 0-pk or Pk-Pk), output is directly dependent on the sample rate, and the overlap. From examination of FIGS. 5A and 7, it can be seen that the delay between sample acquisition, and when corresponding data appears in the ouptut buffer 84 for analysis will depend on three things. First, the time it takes for the sample to propagate from entry into the input frame buffer 76 to the central n addresses of the input frame buffer 76. Second, the frequency domain processing time. And third, the accumulation depth, which will determine how long the accumulator 82 holds an extracted data point before it is forwarded to the ouptut buffer 84.

If the accumulation depth is one, the accumulator will not induce any delay. The processing time can be considered worst case to be ½ of the update rate, for an optimally staged system, (since the computation must be complete in time to handle the two channel pair), or the full update rate for a non-optimally staged system, that is, either 15 or 30 msec. The propagation delay in the input frame buffer 76 will depend on the rate at which samples are loaded into the input frame buffer, and the number of addresses the write pointer of the circular buffer is required to step through before a given sample forms a part of the central 768 addresses which are not discarded during signal reconstruction. In this configuration, any the write pointer will step through at least 640 addresses, and at most 1408 addresses before any given sample becomes part of the output to the feature extractor. The minimum buffer 76 delay is therefore 640/25.6 kHz=25 msec. The worst case delay in the buffer 76 would be 1408/25.6 kHz=55 msec. Different samples will have different delay times between these extremes depending on the acquisition time of the sample relative to the moment the frame buffer 76 content is forwarded to the frequency domain filter 78. Adding 15 or 30 msec frequency domain processing time results in a 70 or 85 msec worst case delay at a 25.6 kHz sampling rate and 30 msec update intervals.

Of course, as decimation stages are added, the effective sample rate goes down and the overlap changes. In general, the elapsed time between the first point appearing in the input that will appear in a given output, is simply the number of new data points, plus ½ of the overlap divided by the effective sample rate, plus the frequency domain processing time. For example, with three decimation stages:
effective sample rate=25.6 kHz divided by 8=3.2 kHz
update period=30 ms
number of new samples=update period*effective sample rate=30 ms*3200 Hz=96
One-Half Overlap=(2048−96)/2=976
Delay=(96+976)/3200+15 msec processing time=350 msec.

For each increase in accumulation depth, an additional update period, i.e. 30 msec in the described embodiment, should be added to the calculated delay. It may be noted that the worst case delay at 25.6 kHz sample rate and 30 msec update period is less than 100 msec, and accordingly, meets industry standard API 670 mentioned above.

The above discussion provides a detailed description of the flow of vibration data through the monitoring system of the invention. Turning now to a description of the design of the frequency domain filter itself, it may be remembered that the time domain signal is advantageously reconstructed after frequency domain filtering. This poses serious difficulties which are overcome in the present invention. For example, it is not possible to simply zero out the frequencies which it is desired to reject before inverse Fourier transforming back into the time domain. Because the original FFT is performed on a sample of limited time duration, this strategy produces large overshoots and discontinuities where the reconstructed segments join together. These overshoots and discontinuities will corrupt the calculations performed by the feature extracter 80 and will produce erroneous event detection as the host analyzes the content of the output buffers 84. Thus, a frequency domain mask filter which comprises a rectangle having a value of zero outside the desired passband and one inside the desired passband does not produce acceptable results. Generation of an appropriate mask is thus critical to an accurate reconstruction of the time domain signal.

It is one aspect of the present invention that the mask is generated by mimicing the behavior, in the frequency domain, of a well designed time domain FIR filter. Although it would be possible to implement such a FIR filter directly in the time domain, the computations involved render this design much more expensive to implement. For example, methods described in text books indicate varying length filters, depending on the desired characteristics. Conventional time domain filter designs also typically prescribe a complex multiplication requiring 4 multiplies and two adds to achieve the filter. A conventional 1024 tap FIR method would require 104,857,600 multiplies and adds per second to perform the filter calculations alone. In contrast, using the frequency domain methods described herein, the performance of a 1024 tap time domain FIR filter can be equaled with a fraction of the processing power. The block processing method herein described, taking full advantage of the properties of real input FFT processing, can accomplish a programmable decimation, flexible corner frequency bandpass, lowpass or highpass filtering, plus the computation of 0-Peak, Peak-Peak, RMS and Smax values on the inputs, in real-time, using a single 80 MHz 24-bit fixed point processor, with a theoretical limit of 40,000,000 multiplies and adds per second.

To model a high performance 1024 tap time domain FIR filter, the filter mask is generated by calculating the actual frequency response of a window designed FIR filter. This process is illustrated by the flow chart of FIG. 8. First, at block 100, the passband or passbands desired are selected. For example, it may be desired to reject all frequencies outside of 2000 Hz to 5000 Hz from the time domain signal. This frequency domain rectangular function is inverse Fourier transformed at block 102 to produce the theoretical impulse response of an ideal bandpass filter having the selected passband. For a bandpass filter coefficients b[i]= $[sin(\omega_{c2}t)-sin(\omega_{c1}t)]/t\pi$ where $\omega_{c2}$=selected highpass frequency divided by the effective sample rate $\omega_{c1}$=selected lowpass frequency divided by the effective sample rate i=0 to N−1 t=i−(N−1)/2

Because optimal filter performance results when the filter order is ½ the length of the FFT frame length, N in the above equations is advantageously equal to 1024 in the described embodiment having a 2048 sample input flame buffer 76. It will be appreciated by those of skill in the art that suitable formulas for filter coefficients may be calculated for any desired filter frequency response. As described above, the single bandpass formula comprises a pair of sinc functions representing a combination of a highpass and a lowpass filter. Filter coefficients for a frequency response of a set of passbands may be easily formed by summing a series of highpass and lowpass filters. Arbitrary frequency responses may be implemented by inverse Fourier transforming the selected frequency response function.

Since b[i] is the ideal impulse response of the desired 1024 tap FIR filter, at block 104 it is multiplied point by point against a window function, thereby producing a widowed set of filter coefficients b'[i]. This is common practice in FIR filter design, and a wide variety of window functions may be used. Which window function is best will depend on the desired compromise between factors such as out of band rejection, ripple, and other filter performance parameters. In one advantageous embodiment of the invention, a Kaiser window is utilized. The β for the Kaiser window may be selected to balance the width of the transition band and the out of band rejection of the filter. For example a β of 9 results in over 80 dB out of band rejection and a transition band of approximately 6 bins. A β of 6.5 gives approximately 65 dB out of band rejection with a transition band of approximately 4 to 5 bins.

At block 106, the windowed filter coefficients may be used to construct the filter mask using a sin series as follows:

$$\text{mask}[n]=\Sigma_{i=0 \text{ to } N-1} b'[i] \sin(2\pi i(n/N))$$

This calculation generates mask values for positive frequencies, and both the positive and the negative frequencies produced by the FFT are modified by the same corresponding mask value. Furthermore, the filter is used as a magnitude only mask, modifying both real and imaginary components of the frequency domain data equally. The aliased frequency of one half the effective sample rate is always zeroed. As long as the same filter frequency response is used, these calculations need not be re-performed, but their results are simply stored in a mask table used during the filtering process. When changes in the frequency response for a given channel is desired, the user may input new corner frequencies for recalculation of the mask.

Figure 8:
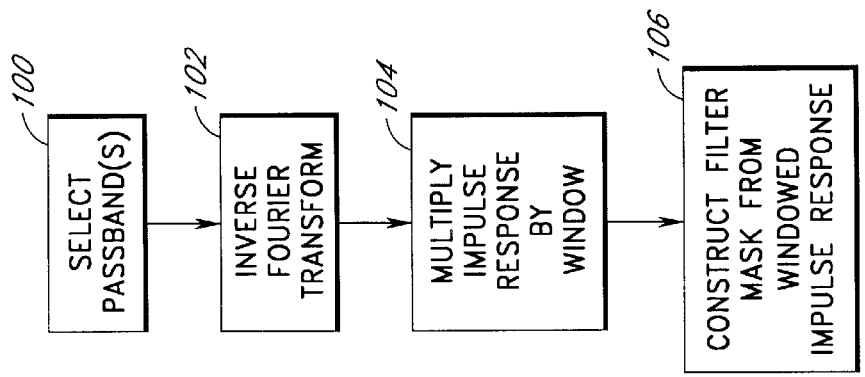
FIG. 8 is a flowchart illustrating the construction of a filter mask for use in the frequency domain filter of FIGS. 5A and 5B.

The above sin series reconstruction will produce a mask function which is similar in shape to the ideal filter function started with at block 100 of FIG. 8. However, the truncated sin series reconstruction will remove any step transitions in the ideal frequency response, and will do so in such a way that the time domain reconstruction of the filtered vibration signal shows no discontinuities or overshoots at the joined ends of the reconstructed segments.

In one advantageous implementation of the invention, 16 bit sample values and 24 bit filter mask values are used. In this implementation, the codecs supply 16 bit samples, but arithmetic internal to the digital signal processor is performed with 24 bit resolution. This helps reduce round-off errors in the filter. In this embodiment, therefore, a large number of sin functions must be calculated when generating the ideal impulse response in the time domain which are preferably of 24 bit resolution. This may be done in a number of different ways. One convenient method uses Taylor Series expansions. Because the Taylor Series expansion for the sin function does not converge quickly for angles larger than $\pi/4$, it is preferable to use symmetries inherent in the sin and cosine to assist this high resolution calculation. In one embodiment, arguments of the sin function are represented such that angles $-2\pi$ to $2\pi$ are mapped onto digital values between −1 and 1. In this representation, the three most significant bits of the positive angle represent the octant where the argument is resident. With this information, a high resolution calculation can be performed quickly using appropriate trigonometric identities and a quickly converging Taylor Series having an argument of less than $\pi/4$.

Table 1 relates effective sample rates with minimum delay times and upper and lower user selectable passband limits which have been found suitable in one embodiment of the invention using a Kaiser windowed bandpass filter with a β of 6.5.

TABLE 1

| Sample Rate | Minimum High pass - 60 + dB stop band | Maximum Lowpass | Decimation Factor | Maximum delay |
|---|---|---|---|---|
| 25600 | 50 | 10000 | $2^0 = 1$ | 70 ms |
| 12800 | 25 | 5000 | $2^1 = 2$ | 110 ms |
| 6400 | 12.5 | 2500 | $2^2 = 4$ | 190 ms |
| 3200 | 6.25 | 1250 | $2^3 = 8$ | 350 ms |
| 1600 | 3.13 | 625 | $2^4 = 16$ | 670 ms |
| 800 | 1.56 | 312.5 | $2^5 = 32$ | 1310 ms |
| 400 | .79 | 156.25 | $2^6 = 64$ | 2590 ms |
| 200 | .40 | 78.125 | $2^7 = 128$ | 5150 ms |

It can be appreciated from the above description that the present invention provides many advantages over prior art vibration data processors. This method uses a fixed length filter, simplifying implementation. Also, a magnitude only mask is used, requiring only two multiplies and zero additions per point, to achieve the filter. Systems in accordance with the invention provide a greater degree of flexibility than analog circuits normally used to perform this type of processing, in addition to unprecedented levels of filter performance. The filter described above will take a signal from the −6 dB point, to more than 60 dB down, in 65 Hz, anywhere in a 10 kHz band. If desired, the post processed analog signal from a D/A converter may be viewed via a processed signal analog output, and the filter settings may be altered digitally, providing heretofore unavailable processing flexibilty.

The foregoing description details certain preferred embodiments of the present invention and describes the best mode contemplated. It will be appreciated, however, that no matter how detailed the foregoing appears in text, the invention can be practiced in many ways. As is also stated above, it should be noted that the use of particular terminology when describing certain features or aspects of the present invention should not be taken to imply that the terminology is being re-defined herein to be restricted to including any specific characteristics of the features or aspects of the invention with which that terminology is associated. The scope of the present invention should therefore be construed in accordance with the appended claims and any equivalents thereof.

What is claimed is:

1. A vibration monitoring system comprising a digital filter having a time domain input coupled to an output of an analog to digital converter and a time domain output coupled to an input of event detection circuitry, wherein said filter has a pipeline delay of less than approximately 100 milliseconds.

2. The vibration monitoring system of claim 1, wherein said digital filter is implemented with a single chip digital signal processor having a maximum throughput of less than approximately 10,000,000 computations per second per channel, and wherein each channel is sampled at a rate of least approximately 25.6 kHz.

3. The vibration monitoring system of claim 2, wherein said digital filter comprises a frequency domain filter.

4. A vibration data processor, comprising:
 a frequency domain filter for filtering digital samples of a vibration transducer signal;
 a mask generator coupled to said frequency domain filter for creating and storing filter masks used by said frequency domain filter.

5. The vibration data processor of claim 4, additionally comprising a user input device coupled to said mask generator for user specification of one or more frequency response characteristics of said frequency domain filter.

6. The vibration data processor of claim 4, additionally comprising a digital pre-processor configured to receive time domain data samples, and coupled to said frequency domain filter so as to forward pre-processed time domain data samples to said frequency domain filter.

7. The vibration data processor of claim 6, wherein said pre-processor comprises a plurality of decimation stages.

8. The vibration data processor of claim 7, additionally comprising a user input device coupled to said pre-processor so as to select a subset of said plurality of decimation stages for operation.

9. A method of analyzing vibration data comprising the steps of:
 selecting a size of a data accumulator;
 storing measured vibrational features in said accumulator;
 when said accumulator is full, updating the content of an output buffer with the content of said accumulator; and
 calculating overall vibration parameters using the content of said output buffer.

10. The method of claim 9, additionally comprising the step of selecting a size of said output buffer such that said size is an integer multiple of said size of said accumulator.

11. A vibration data processor comprising an output buffer of user selectable length and an accumulator of user selectable depth, wherein said accumulator receives vibrational data at first intervals from the output of a digital vibration data filter, wherein said accumulator stores said data, a maximum amount of data storable therein being defined by said user selectable depth; and wherein said accumulator is coupled to said output buffer so as to periodically update said output buffer at second intervals when said accumulator is full.

12. The vibration data processor of claim 11, wherein said digital vibration data filter comprises a frequency domain filter.

13. A vibration data processor, comprising:
 a pre-processor comprising a user selectable number of decimation stages;
 a user configurable frequency domain filter coupled to receive data from said pre-processor; and
 an output buffer of user selectable length coupled to receive vibration data from said frequency domain filter.

14. The vibration data processor of claim 13, additionally comprising a feature extractor coupled between said frequency domain filter and said output buffer.

15. The vibration data processor of claim 14, additionally comprising an accumulator of user selectable depth coupled between said feature extractor and said output buffer.

* * * * *